United States Patent
Snow et al.

(10) Patent No.: US 8,764,624 B2
(45) Date of Patent: Jul. 1, 2014

(54) INDUCTIVELY POWERED REMOTELY ADJUSTABLE GASTRIC BANDING SYSTEM

(75) Inventors: Sean Snow, Carpinteria, CA (US); Janel A. Birk, Oxnard, CA (US); Robert Stone, Sunnyvale, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 670 days.

(21) Appl. No.: 12/712,883

(22) Filed: Feb. 25, 2010

(65) Prior Publication Data

US 2011/0207995 A1 Aug. 25, 2011

(51) Int. Cl.
*A61F 2/00* (2006.01)
*A61F 13/00* (2006.01)

(52) U.S. Cl.
USPC ............ 600/37; 713/310; 600/488; 606/65; 606/157; 606/201; 606/202; 606/153; 604/65

(58) Field of Classification Search
USPC .......... 600/37; 713/310; 363/60; 607/2, 115, 607/60–62, 65; 128/903
See application file for complete search history.

(56) References Cited

U.S. PATENT DOCUMENTS

| | | | |
|---|---|---|---|
| 2,163,048 A | 6/1939 | McKee | |
| 3,667,081 A | 6/1972 | Burger | |
| 3,840,018 A | 10/1974 | Heifetz | |
| 4,118,805 A | 10/1978 | Reimels | |
| 4,157,713 A | 6/1979 | Clarey | |
| 4,340,083 A | 7/1982 | Cummins | |
| 4,406,656 A | 9/1983 | Hattler et al. | |
| 4,450,375 A | 5/1984 | Siegal | |
| 4,592,339 A | 6/1986 | Kuzmak et al. | |
| 4,592,355 A | 6/1986 | Antebi | |
| 4,601,713 A | 7/1986 | Fuqua | |
| 4,671,351 A | 6/1987 | Rappe | |
| 4,696,288 A | 9/1987 | Kuzmak et al. | |
| 4,760,837 A | 8/1988 | Petit | |
| 4,881,939 A | 11/1989 | Newman | |
| 4,883,467 A | 11/1989 | Franetzki et al. | |
| 4,944,659 A | 7/1990 | Labbe | |
| 5,045,060 A | 9/1991 | Melsky et al. | |
| 5,074,868 A | 12/1991 | Kuzmak | |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Maxim Low-Power Triple-Output TFT LCD DC-DC Converter Data Sheet, 19-1795; Rev 0; Nov. 2000.*

(Continued)

*Primary Examiner* — Christine Matthews
*Assistant Examiner* — Sunita Reddy
(74) *Attorney, Agent, or Firm* — Gordon & Jacobson, PC

(57) ABSTRACT

A power management system provides wireless power to operate components of a remotely adjustable gastric banding system. The power management system comprises an external power component transmitting power, and an implantable power management component receiving power and converting the power for use in powering one or more components of the remotely adjustable gastric banding system, such as a pump. The internal power management component and the external power component may be tunable. By utilizing the power management system, implantable batteries may be eliminated.

5 Claims, 4 Drawing Sheets

(56) References Cited

U.S. PATENT DOCUMENTS

| | | | |
|---|---|---|---|
| 5,089,019 | A | 2/1992 | Grandjean |
| 5,120,313 | A | 6/1992 | Elftman |
| 5,160,338 | A | 11/1992 | Vincent |
| 5,226,429 | A | 7/1993 | Kuzmak |
| 5,259,399 | A | 11/1993 | Brown |
| 5,326,349 | A | 7/1994 | Baraff |
| 5,343,894 | A | 9/1994 | Frisch et al. |
| 5,360,445 | A | 11/1994 | Goldowsky |
| 5,449,368 | A | 9/1995 | Kuzmak |
| 5,458,568 | A | 10/1995 | Racchini et al. |
| 5,496,312 | A | 3/1996 | Klicek |
| 5,535,752 | A | 7/1996 | Halperin et al. |
| 5,554,113 | A | 9/1996 | Novak et al. |
| 5,562,714 | A | 10/1996 | Grevious et al. ............ 607/32 |
| 5,601,604 | A | 2/1997 | Vincent |
| 5,658,298 | A | 8/1997 | Vincent et al. |
| 5,676,162 | A | 10/1997 | Larson, Jr. et al. |
| 5,733,257 | A | 3/1998 | Sternby |
| 5,748,200 | A | 5/1998 | Funahashi |
| 5,759,015 | A | 6/1998 | Van Lintel et al. |
| 5,766,232 | A | 6/1998 | Grevious et al. |
| 5,807,311 | A | 9/1998 | Palestrant |
| 5,861,014 | A | 1/1999 | Familoni |
| RE36,176 | E | 3/1999 | Kuzmak |
| 5,910,149 | A | 6/1999 | Kuzmak |
| 5,938,669 | A | 8/1999 | Klaiber et al. |
| 6,024,340 | A | 2/2000 | Lazarus et al. |
| 6,024,704 | A | 2/2000 | Meador et al. |
| 6,042,345 | A | 3/2000 | Bishop et al. |
| 6,067,991 | A | 5/2000 | Forsell |
| 6,074,341 | A | 6/2000 | Anderson et al. |
| 6,083,249 | A | 7/2000 | Familoni |
| 6,102,678 | A | 8/2000 | Peclat |
| 6,102,922 | A | 8/2000 | Jakobsson et al. |
| 6,164,933 | A | 12/2000 | Tani et al. |
| 6,210,347 | B1 | 4/2001 | Forsell |
| 6,221,024 | B1 | 4/2001 | Miesel |
| 6,306,088 | B1 | 10/2001 | Krausman et al. |
| 6,327,503 | B1 | 12/2001 | Familoni |
| 6,417,750 | B1 | 7/2002 | Sohn |
| 6,432,040 | B1 | 8/2002 | Meah |
| 6,439,539 | B1 | 8/2002 | Powell |
| 6,450,173 | B1 | 9/2002 | Forsell |
| 6,450,946 | B1 | 9/2002 | Forsell |
| 6,450,987 | B1 | 9/2002 | Kramer |
| 6,453,907 | B1 | 9/2002 | Forsell |
| 6,454,699 | B1 | 9/2002 | Forsell |
| 6,454,700 | B1 | 9/2002 | Forsell |
| 6,454,701 | B1 | 9/2002 | Forsell |
| 6,454,785 | B2 | 9/2002 | De Hoyos Garza |
| 6,460,543 | B1 * | 10/2002 | Forsell ............ 128/898 |
| 6,461,293 | B1 | 10/2002 | Forsell |
| 6,463,935 | B1 | 10/2002 | Forsell |
| 6,464,628 | B1 | 10/2002 | Forsell |
| 6,470,892 | B1 | 10/2002 | Forsell |
| 6,475,136 | B1 | 11/2002 | Forsell |
| 6,511,490 | B2 | 1/2003 | Robert |
| 6,527,701 | B1 | 3/2003 | Sayet et al. |
| 6,547,801 | B1 | 4/2003 | Dargent et al. |
| 6,579,301 | B1 | 6/2003 | Bales et al. |
| 6,676,674 | B1 | 1/2004 | Dudai |
| 6,681,135 | B1 | 1/2004 | Davis et al. |
| 6,685,668 | B1 | 2/2004 | Cho et al. |
| 6,691,047 | B1 | 2/2004 | Fredericks |
| 6,715,731 | B1 | 4/2004 | Post et al. |
| 6,729,600 | B2 | 5/2004 | Mattes et al. |
| 6,754,527 | B2 | 6/2004 | Stroebel et al. ............ 607/5 |
| 6,811,136 | B2 | 11/2004 | Eberhardt et al. |
| 6,820,651 | B2 | 11/2004 | Seuret et al. |
| 6,834,201 | B2 | 12/2004 | Gillies et al. |
| 6,871,090 | B1 | 3/2005 | He et al. ............ 607/2 |
| 6,889,086 | B2 | 5/2005 | Mass et al. |
| 6,940,467 | B2 | 9/2005 | Fischer et al. ............ 343/850 |
| 6,966,875 | B1 | 11/2005 | Longobardi |
| 7,017,583 | B2 | 3/2006 | Forsell |
| 7,017,883 | B2 | 3/2006 | Bayer et al. |
| 7,021,147 | B1 | 4/2006 | Subramanian et al. |
| 7,037,344 | B2 | 5/2006 | Kagan et al. |
| 7,040,349 | B2 | 5/2006 | Moler et al. |
| 7,048,519 | B2 | 5/2006 | Fong et al. |
| 7,058,434 | B2 | 6/2006 | Wang et al. |
| 7,060,080 | B2 | 6/2006 | Bachmann |
| 7,066,486 | B2 | 6/2006 | Birk |
| 7,118,526 | B2 | 10/2006 | Egle |
| 7,128,750 | B1 | 10/2006 | Stergiopulos |
| 7,191,007 | B2 | 3/2007 | Desai et al. |
| 7,198,250 | B2 | 4/2007 | East |
| 7,204,821 | B1 | 4/2007 | Clare et al. |
| 7,206,637 | B2 | 4/2007 | Salo |
| 7,238,191 | B2 | 7/2007 | Bachmann |
| 7,282,023 | B2 | 10/2007 | Frering |
| 7,284,966 | B2 | 10/2007 | Xu et al. |
| 7,288,064 | B2 | 10/2007 | Boustani et al. |
| 7,310,557 | B2 | 12/2007 | Maschino et al. |
| 7,311,503 | B2 | 12/2007 | Van Lintel et al. |
| 7,311,716 | B2 | 12/2007 | Byrum |
| 7,311,717 | B2 | 12/2007 | Egle |
| 7,314,443 | B2 | 1/2008 | Jordan et al. |
| 7,338,433 | B2 | 3/2008 | Coe |
| 7,351,198 | B2 | 4/2008 | Byrum et al. |
| 7,351,240 | B2 | 4/2008 | Hassler, Jr. et al. |
| 7,353,747 | B2 | 4/2008 | Swayze et al. |
| 7,364,542 | B2 | 4/2008 | Jambor et al. |
| 7,366,571 | B2 | 4/2008 | Armstrong |
| 7,367,340 | B2 | 5/2008 | Nelson et al. |
| 7,367,937 | B2 | 5/2008 | Jambor et al. |
| 7,374,565 | B2 | 5/2008 | Hassler, Jr. et al. |
| 7,390,294 | B2 | 6/2008 | Hassler, Jr. |
| 7,396,353 | B2 | 7/2008 | Lorenzen et al. |
| 7,416,528 | B2 | 8/2008 | Crawford et al. |
| 7,481,763 | B2 | 1/2009 | Hassler et al. |
| 7,500,944 | B2 | 3/2009 | Byrum et al. |
| 7,530,943 | B2 | 5/2009 | Lechner |
| 7,594,885 | B2 | 9/2009 | Byrum |
| 7,599,743 | B2 | 10/2009 | Hassler, Jr. et al. |
| 7,599,744 | B2 | 10/2009 | Giordano et al. |
| 7,601,162 | B2 | 10/2009 | Hassler, Jr. et al. |
| 7,615,001 | B2 | 11/2009 | Jambor et al. |
| 7,618,365 | B2 | 11/2009 | Jambor et al. |
| 7,658,196 | B2 | 2/2010 | Ferreri et al. |
| 7,699,770 | B2 | 4/2010 | Hassler, Jr. et al. |
| 7,727,141 | B2 | 6/2010 | Hassler, Jr. et al. |
| 7,758,493 | B2 | 7/2010 | Gingras |
| 7,766,815 | B2 | 8/2010 | Ortiz |
| 7,771,439 | B2 | 8/2010 | Griffiths |
| 7,775,215 | B2 | 8/2010 | Hassler, Jr. et al. |
| 7,775,966 | B2 | 8/2010 | Dlugos et al. |
| 7,794,386 | B2 | 9/2010 | Brooks |
| 7,811,298 | B2 | 10/2010 | Birk |
| 7,844,342 | B2 | 11/2010 | Dlugos et al. |
| 2001/0011543 | A1 | 8/2001 | Forsell |
| 2002/0072780 | A1 | 6/2002 | Foley |
| 2002/0091395 | A1 | 7/2002 | Gabbay |
| 2002/0095181 | A1 | 7/2002 | Beyar |
| 2002/0139208 | A1 | 10/2002 | Yatskov |
| 2002/0193679 | A1 | 12/2002 | Malave et al. |
| 2002/0198548 | A1 | 12/2002 | Robert |
| 2003/0019498 | A1 | 1/2003 | Forsell |
| 2003/0045775 | A1 | 3/2003 | Forsell |
| 2003/0055311 | A1 | 3/2003 | Neukermans et al. |
| 2003/0066536 | A1 | 4/2003 | Forsell |
| 2003/0073880 | A1 | 4/2003 | Polsky et al. |
| 2003/0158569 | A1 | 8/2003 | Wazne |
| 2003/0191433 | A1 | 10/2003 | Prentiss |
| 2003/0208212 | A1 | 11/2003 | Cigaina |
| 2004/0000843 | A1 | 1/2004 | East |
| 2004/0044332 | A1 | 3/2004 | Stergiopulos |
| 2004/0059393 | A1 | 3/2004 | Policker et al. |
| 2004/0133219 | A1 | 7/2004 | Forsell |
| 2004/0147816 | A1 | 7/2004 | Policker et al. |
| 2004/0148034 | A1 | 7/2004 | Kagan et al. |
| 2004/0153106 | A1 | 8/2004 | Dudai |
| 2004/0162595 | A1 | 8/2004 | Foley |
| 2004/0215159 | A1 | 10/2004 | Forsell |

(56) References Cited

U.S. PATENT DOCUMENTS

| | | |
|---|---|---|
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0143765 A1 | 6/2005 | Bachmann et al. |
| 2005/0143766 A1 | 6/2005 | Bachmann et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0216042 A1 | 9/2005 | Gertner |
| 2005/0228415 A1 | 10/2005 | Gertner |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler et al. |
| 2005/0267533 A1 | 12/2005 | Gertner |
| 2005/0277899 A1 | 12/2005 | Conlon et al. |
| 2005/0283041 A1 | 12/2005 | Egle |
| 2005/0288739 A1 | 12/2005 | Hassler |
| 2005/0288740 A1 | 12/2005 | Hassler |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0161186 A1 | 7/2006 | Hassler, Jr. et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler et al. |
| 2006/0189888 A1* | 8/2006 | Hassler et al. ............... 600/561 |
| 2006/0189889 A1 | 8/2006 | Gertner |
| 2006/0195139 A1 | 8/2006 | Gertner |
| 2006/0197412 A1 | 9/2006 | Rasmussen |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212053 A1 | 9/2006 | Gertner |
| 2006/0235448 A1 | 10/2006 | Roslin et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. et al. |
| 2006/0264699 A1 | 11/2006 | Gertner |
| 2006/0276812 A1 | 12/2006 | Hill et al. |
| 2007/0015954 A1 | 1/2007 | Dlugos |
| 2007/0015955 A1 | 1/2007 | Tsonton |
| 2007/0016262 A1 | 1/2007 | Gross et al. |
| 2007/0027356 A1 | 2/2007 | Ortiz |
| 2007/0078476 A1 | 4/2007 | Hull et al. |
| 2007/0097719 A1* | 5/2007 | Parramon et al. ............... 363/72 |
| 2007/0125826 A1 | 6/2007 | Shelton |
| 2007/0156013 A1 | 7/2007 | Birk ............... 600/37 |
| 2007/0167672 A1 | 7/2007 | Dlugos et al. |
| 2007/0185462 A1 | 8/2007 | Byrum |
| 2007/0218083 A1 | 9/2007 | Brooks |
| 2007/0232848 A1 | 10/2007 | Forsell |
| 2007/0235083 A1 | 10/2007 | Dlugos |
| 2007/0250085 A1 | 10/2007 | Bachmann et al. |
| 2007/0250086 A1 | 10/2007 | Wiley et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2008/0009680 A1 | 1/2008 | Hassler, Jr. |
| 2008/0015406 A1 | 1/2008 | Dlugos et al. |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0166028 A1 | 7/2008 | Turek et al. |
| 2008/0221598 A1 | 9/2008 | Dlugos et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0270904 A1 | 10/2009 | Birk ............... 606/192 |
| 2009/0306462 A1 | 12/2009 | Lechner |
| 2009/0312785 A1 | 12/2009 | Stone et al. |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0211145 A1* | 8/2010 | Cantatore ............... 607/116 |
| 2010/0228080 A1 | 9/2010 | Tavori et al. |
| 2010/0249803 A1 | 9/2010 | Griffiths |
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk |

FOREIGN PATENT DOCUMENTS

| | | |
|---|---|---|
| DE | 4225524 | 2/1994 |
| DE | 10020688 | 12/2000 |
| EP | 0119596 | 9/1984 |
| EP | 0230747 | 8/1987 |

(56) References Cited

FOREIGN PATENT DOCUMENTS

| | | |
|---|---|---|
| EP | 0611561 | 8/1994 |
| EP | 0695558 | 2/1996 |
| EP | 0867808 | 11/1998 |
| EP | 1072282 | 1/2001 |
| EP | 1396242 | 3/2004 |
| EP | 1396243 | 3/2004 |
| EP | 1491167 | 12/2004 |
| EP | 1547549 | 6/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 89/11701 | 11/1989 |
| WO | WO 00/09047 | 2/2000 |
| WO | WO 00/09048 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 01/70131 | 9/2001 |
| WO | WO 02/26317 | 4/2002 |
| WO | WO 02/053093 | 7/2002 |
| WO | WO 02/065948 | 8/2002 |
| WO | WO 03/077191 | 9/2003 |
| WO | WO 03/105732 | 12/2003 |
| WO | WO 2004/014245 | 2/2004 |
| WO | WO 2004/019671 | 3/2004 |
| WO | WO 2005/007232 | 1/2005 |
| WO | WO 2005/009305 | 2/2005 |
| WO | WO 2005/087147 | 9/2005 |
| WO | WO 2005/094447 | 10/2005 |
| WO | WO 2006/083885 | 8/2006 |
| WO | WO 2006/108203 | 10/2006 |
| WO | WO 2008/109300 | 9/2008 |
| WO | WO 2009/132127 | 10/2009 |

OTHER PUBLICATIONS

Gregoire, A Compact Switched-Capacitor Regulated Charge Pump Power Supply, IEEE Journal of Solid-State Circuits, Vol. 41, No. 8, Aug. 2006, pp. 1944-1953.*

Corno et al.; "A new implantable device for telemetric control of pulmonary blood flow," New Ideas; received Apr. 24, 2004; received in revised form Jul. 12, 2002; accepted Jul. 22, 2002.

Corno et al.; "FloWatchTM in clipped and inclipped position," Interact Cardio Vase Thorac Surg 2002; 1:46-49.

BioEnterics Lap-Band Adjustable Gastric Banding System, Inamed Health, pub. Aug. 28, 2003 pp. 1-115.

Iverson et al.; "Recent Advances in Microscale Pumping Technologies: A Review and Evaluation"; Microfluid Nanofluid; vol. 5; pp. 145-174; Feb. 19, 2008.

* cited by examiner

INDUCTIVELY POWERED REMOTELY ADJUSTABLE GASTRIC BANDING SYSTEM

FIELD

The present invention generally relates to medical systems and apparatus and uses thereof for treating obesity and/or obesity-related diseases, and more specifically, relates to remotely adjustable gastric banding systems.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, the food held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion, for example, by means of an implantable pump, the effective size of the gastric band can be adjusted to provide a tighter or looser constriction. The level of constriction is related to the amount of fluid in the gastric band system. The level of constriction is also related to the pressure within the gastric band system.

It would be desirable to inductively transfer power to operate a pump, a pressure sensor, or other implantable components of a gastric banding system, for example, in order to eliminate implanted batteries or other implanted power sources.

Various approaches for inductive powering have previously been attempted. A circuit arrangement and method for obtaining power from an electromagnetic field is disclosed in U.S. Pat. No. 6,940,467 to Fischer et al. Various antenna arrangements for mobile communication are disclosed in U.S. Pat. No. 7,058,434 to Wang et al. A magnetic field strength regulator for an implantable device is disclosed in U.S. Pat. No. 5,562,714 to Grevious et al. A method and apparatus for altering the quality factor of an implantable antenna is disclosed in U.S. Pat. No. 5,766,232 to Grevious et al.

Other implantable devices have relied at least partially on implanted battery power. An implantable spinal cord stimulation system is disclosed in U.S. Pat. No. 6,871,090 to He et al. However, the system of He requires an implanted battery. A cardiac monitoring system is disclosed in U.S. Pat. No. 6,754,527 to Stroebel et al. The Stroebel design utilizes an implanted battery to produce sufficient voltage for operation of the system, and is directed to reducing noise in the implantable device.

It remains desirable to power implantable components of a gastric banding system via inductive coupling to an external power source. Thus, power management for implantable gastric banding systems is described herein.

SUMMARY

Generally described herein is inductive powering for implantable components of remotely adjustable gastric banding systems, and methods of use thereof. The apparatus, systems and methods described herein aid in facilitating obesity control and/or treating obesity-related diseases, and may be non-invasive once implanted.

In an exemplary embodiment, an implantable device uses inductive coupling to adjust a circumference of a gastric band. The implantable device comprises an antenna for receiving power from a remote device, a converter for converting the power to a low voltage direct current, and a charge pump for converting the low voltage direct current to a voltage signal. The charge pump is capable of being turned off using a telemetric signal received from the remote device. The implantable device further comprises an electromechanical device, coupled to the gastric band, for increasing and decreasing the circumference of the gastric band using the voltage signal received from the charge pump.

In another exemplary embodiment, a system facilitates obesity control. The system comprises an implantable gastric banding device including an inflatable member for containing fluid and restricting a patient's cardia, an implantable fluid reservoir, and an implantable pump unit for controlling pressure within the inflatable member. The implantable pump unit is in communication with the fluid reservoir and the gastric banding device via tubing.

The system further comprises an implantable access port coupled to the implantable pump unit. The implantable pump unit is in communication with the fluid reservoir and the gastric banding device via tubing.

The system further comprises a pressure sensor disposed at least partially within the tubing, and a power management system for providing power to the implantable pump unit and the pressure sensor. The power management system comprises an external remote control device capable of communicating with and powering an implantable power management component and a pressure sensor via inductive coupling. The power management system further comprises the implantable power management component. The implantable power management component supplies power received from the external remote control device to the implantable pump unit.

In another exemplary embodiment, a power management system for a remotely adjustable gastric banding system comprises an external power component. The external power component comprises an inductive power transmitter, a switchable tuning circuit coupled to the inductive power transmitter, a driver circuit coupled to the switchable tuning circuit, and a first microcontroller coupled to the driver circuit and to a first communication circuit. The first microcontroller is configured to govern operation of the external power component. The external power component further comprises a first communication antenna coupled to the first communication circuit.

The power management system further comprises a power management component. The power management component comprises a tunable inductive power receiver for receiving power from the electromagnetic power signal, and a voltage rectifier coupled to the inductive power receiver. The voltage rectifier outputs a direct current (DC) voltage responsive to an alternating current (AC) voltage received from the inductive power receiver.

The power management component further comprises a voltage conditioner coupled to the voltage rectifier, a sampling circuit coupled to the voltage rectifier for assessing an amount of power received at the inductive power receiver, a voltage regulator coupled to the voltage conditioner for supplying at least one fixed DC voltage, and a second microcontroller coupled to the sampling circuitry. The second microcontroller is coupled to a second communication circuit coupled to a second communication antenna. The second microprocessor is configured to report an amount of power received at the inductive power receiver to the external remote control device via the electromagnetic communication signal.

The power management component further comprises a positive high voltage generator coupled to the voltage regulator and to the second microcontroller. The positive high voltage generator is configured to generate a positive output voltage of at least about 60 volts responsive to a command from the second microcontroller.

The power management component further comprises a negative high voltage generator coupled to the voltage regulator and to the second microcontroller. The negative high voltage generator is configured to generate a negative output voltage of at least about 60 volts responsive to a command from the second microcontroller. The positive output voltage and the negative output voltage are utilized to operate the implantable pump unit.

DETAILED DESCRIPTION

The present invention generally provides inductive powering and remote control of remotely adjustable gastric banding systems, for example, for treatment of obesity and obesity related conditions.

Figure 1A:
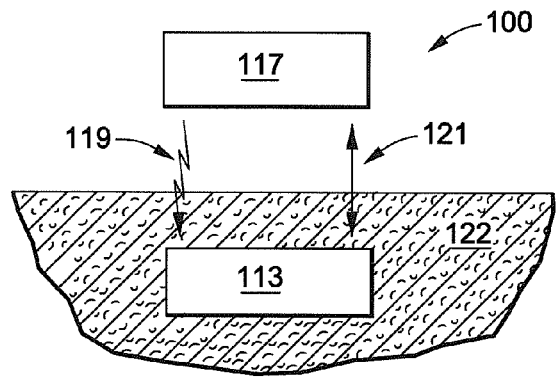
FIG. 1A illustrates an overall schematic view of an example configuration of components according to an embodiment of the present invention.

Turning now to FIG. 1A, a power management component 100 in accordance with one embodiment of the present invention generally includes an external power component 117 and an implantable power management component 113. When the power management component 113 is implanted within a tissue 122, power may be wirelessly delivered to the power management component 113 from the external power component 117 via an electromagnetic power signal 119 transferred through the tissue 122.

Two-way communications, for example, command communication, feedback, and/or the like, between the external power component 117 and the power management component 113 may take place via an electromagnetic communication signal 121. In one example, the electromagnetic signals 119 and 121 share a common frequency. In various other examples, the electromagnetic signals 119 and 121 are operative on different frequencies. The command communication, feedback, and/or the like can be configured, for example, to take place at about 402-406 MHz while the power transmission, for example, takes place at about 400 kHz. This communication adheres to the frequency and power standards set by the Medical Implant Communications Service. Other communication and/or power frequency ranges may be utilized, as desired. To ensure accuracy, communication and control commands may be verified prior to data reporting or command implementation, for example, by error checking and/or correction algorithms.

Figure 1B:
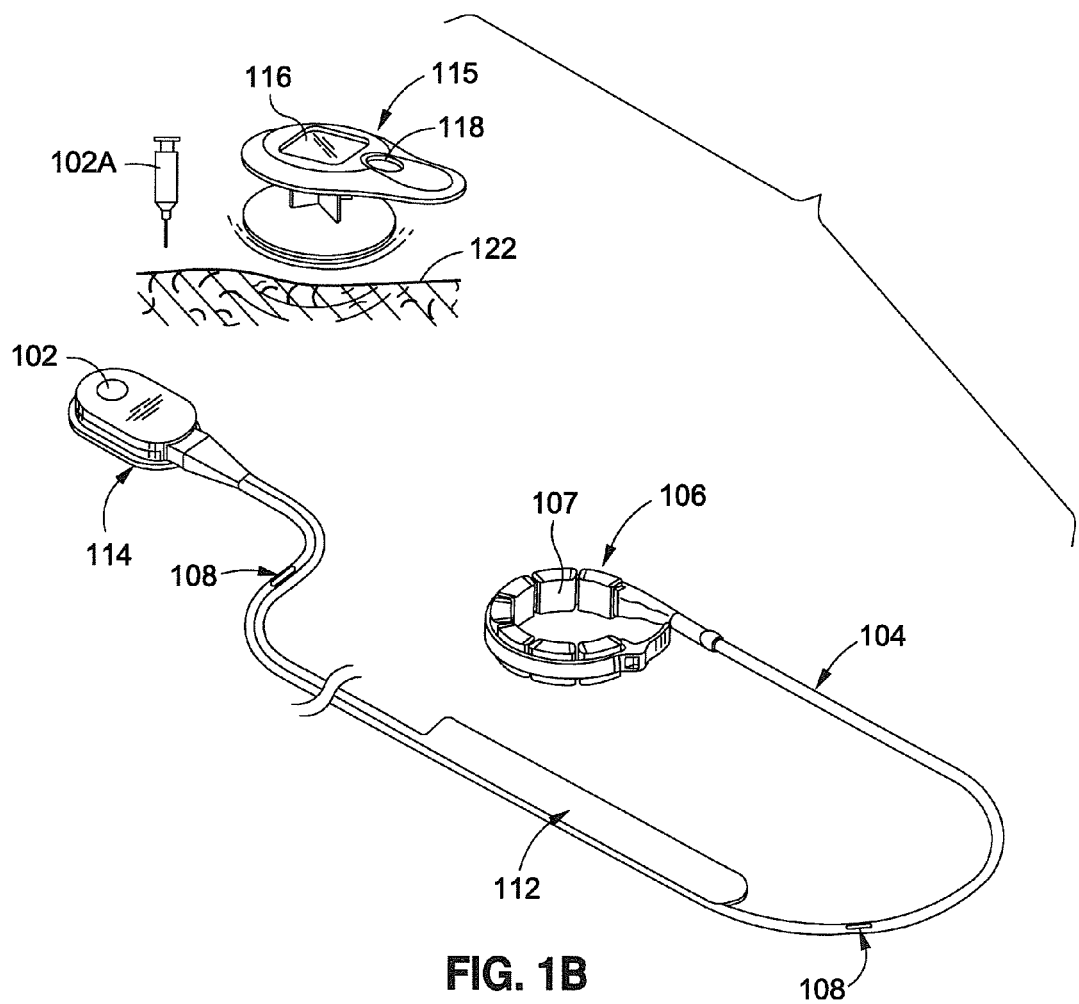
FIG. 1B illustrates an overall schematic view of an example configuration of components according to an embodiment of the present invention.

Turning now to FIG. 1B, in accordance with one embodiment of the present invention, the power management component 100 of FIG. 1A may be coupled to and/or integrated with components of a remotely adjustable gastric banding system. For example, the external power component 117 (not shown in FIG. 1B) may be contained within and/or coupled to a remote controller unit 115. For example, the external power component 117 may be a subcomponent of the remote controller unit 115. Similarly, the power management component 113 may be contained within and/or coupled to a high precision pump unit 114. For example, the power management component 113 may be a subcomponent of the high precision pump unit 114. Moreover, the power management component 113 and/or the external power component 117 may also be coupled to and/or contained within other components of a remotely adjustable gastric banding system, as desired. Additionally, the power management component 113 may comprise various voltage multipliers, voltage regulators, voltage conditioners, and/or the like, as desired, in order to convert power received via the electromagnetic power signal 119 into an electrical output having a desired voltage, a desired current, a desired waveform, and/or other desired electrical properties in order to suitably power other components of the remotely adjustable gastric banding system.

The remotely adjustable gastric banding system may further comprise an access port 102, a tubing 104, a gastric band 106 having at least one inflatable member 107, a pressure sensor 108, and a reservoir 112.

The access port 102 may be used, for example, with a hypodermic needle 102A, to fill and drain the gastric band 106, for example, responsive to pressure measured by the pressure sensor 108 and communicated to the remote controller unit 115. The access port 102 and/or the hypodermic needle 102A may also be used in the event of a loss of power or unavailability of the remote controller unit 115.

Each of the components of the remotely adjustable gastric banding system, other than the remote controller unit 115 and/or the external power component 117, is implantable in a patient using conventional surgical techniques. The high precision pump unit 114 can be used to complement or replace the access port 102 for adjusting inflation of the gastric band 106, for example, responsive to pressure measured by the pressure sensor 108.

With reference to FIGS. 1A and 1B, in various example embodiments, inductive supply of all operating power utilized by implantable components of a gastric banding system is disclosed. When compared to previous approaches incorporating implantable batteries to partially and/or fully power implantable components, the concepts of the present invention eliminate the need to provide an implantable battery and/or change the implantable battery, via invasive surgery or otherwise. Additionally, when compared to previous approaches utilizing fixed inductive coupling, the concepts of the present invention enable tuning, detuning, adjusting, modulating, and/or regulating the power and/or communicative couplings between components.

Figure 2A:
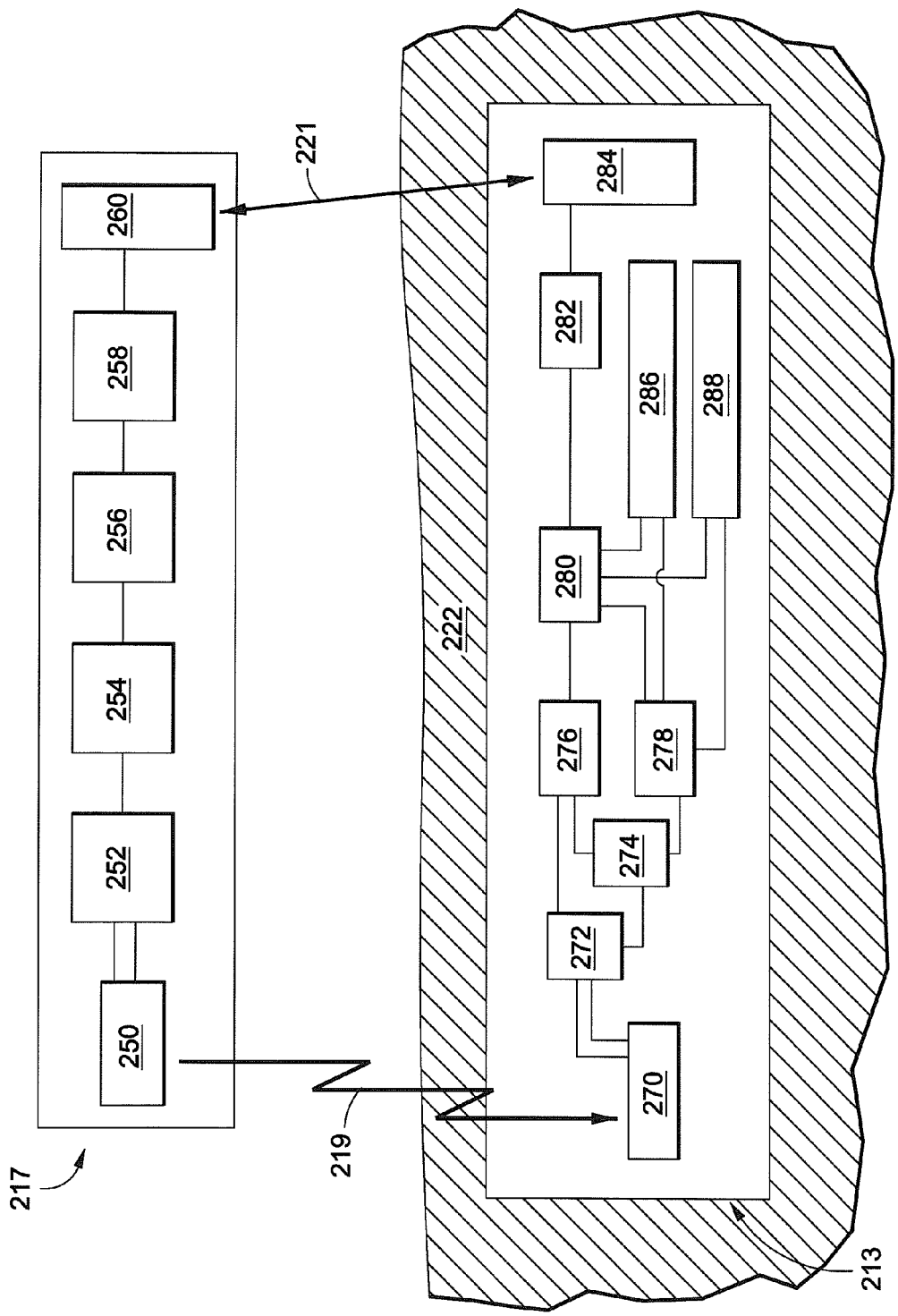
FIG. 2A illustrates a block diagram of an external power component and an implantable power management component in an example configuration of components according to an embodiment of the present invention.

Turning now to FIG. 2A, in an example embodiment, an external power component 217 generally comprises an inductive power transmitter 250, a switchable tuning circuit 252, a driver circuit 254, a microcontroller 256, a communication circuit 258, and a communication antenna 260. The external power component 217 delivers wireless power for use by the power management component 213 and/or other components of the remotely adjustable gastric banding system via an electromagnetic power signal 219. The external power component 217 also communicates with the power management component 213 and/or other components of the remotely adjustable gastric banding system via an electromagnetic communication signal 221.

In an example embodiment, the inductive power transmitter 250 comprises an inductive antenna. The inductive power transmitter 250 may be configured to deliver power via mutual induction, resonant induction, and/or any other suitable wireless power transmission method and/or technique. Further, the inductive power transmitter 250 may be operative over a range of frequencies. In various example embodiments, the inductive power transmitter 250 is operative over a range of frequencies from about 400 kHz to about 27 MHz. Moreover, the inductive power transmitter 250 may be operative at any suitable frequency to transfer power to implanted components of the remotely adjustable gastric banding system without excessive heating of a patient's tissue 222. The inductive power transmitter 250 is coupled to the switchable tuning circuit 252.

In an example embodiment, the switchable tuning circuit 252 is configured to provide a power signal to the inductive power transmitter 250. The switchable tuning circuit 252 may comprise various transistors, chips, and/or other components in order to vary one or more characteristics of the power signal. For example, the switchable tuning circuit 252 is configured to vary the central frequency of the power signal. The switchable tuning circuit 252 may also be configured to vary the quality factor of the power signal, or other parameters of the power signal. By varying various parameters of the power signal, for example, the central frequency, the quality factor, and/or the like, the switchable tuning circuit 252 may be configured to deliver a variable amount of power to the power management component 213.

Additionally, the switchable tuning circuit 252 may vary a parameter of the power signal responsive to feedback received from the power management component 213. For example, the power management component 213 may report having received a first amount of power, such as 100 milliwatts. However, the desired amount of power delivered to the power management component 213 may be different than the reported power received, for example 500, milliwatts. Under the guidance of the microcontroller 256, the switchable tuning circuit 252 may then iteratively vary one or more parameters of the power signal, and the external power component 217 may receive corresponding feedback from the power management component 213, until the desired level of power intended to be delivered to the power management component 213 is reported as having been received at the power management component 213. The switchable tuning circuit 252 is coupled to the driver circuit 254.

The driver circuit 254 delivers operating power to and/or controls operation of the switchable tuning circuit 252 responsive to signals from the microcontroller 256. The driver circuit 254 also provides power configured to drive the inductive power transmitter 250. The driver circuit 254 is coupled to the microcontroller 256.

The microcontroller 256 governs operation of the external power component 217. In an exemplary embodiment, the microcontroller 256 comprises a programmable microcontroller, for example, one or more of the following: a microcontroller from the Texas Instruments brand MSP430 or CC430 families; a microcontroller from the MicroChip brand PIC16 or PIC18 families; or a microcontroller from the Freescale brand MC9 family. Moreover, the microcontroller 256 may be configured to monitor, control, and/or otherwise govern operation of the external power component 217, for example, responsive to user input, responsive to information received from the power management component 213 via the electromagnetic communication signal 221, and/or the like.

For example, in certain embodiments, the microcontroller 256 may assess a signal received from the power management component 213 responsive to power delivered by the inductive power transmitter 250. The power management component 213 may measure, assess, and/or otherwise monitor and/or characterize the amount of power received from the external power component 217. The power management component 213 may then report the amount of power received or other information to the external power component 217. The microcontroller 256 may assess the reported amount of power received, and may then issue commands intended to vary a characteristic of the power transmitted by the inductive power transmitter 250. In this manner, the amount of power transmitted and/or received may be varied, adjusted, and/or otherwise controlled in order to provide a suitable amount of power to the power management component 213. In this manner, the microcontroller 256 can more efficiently utilize a power source, for example, battery power of the remote controller unit 115, as excessive energy delivered through the patient's tissue 222 may be reduced and/or eliminated. The microcontroller 256 is coupled to the communication circuit 258.

The communication circuit 258 is configured to send and receive signals to and from the power management component 213 via the communication antenna 260. In an exemplary embodiment, the communication circuit 258 comprises a low-power RF transceiver, for example, a Texas Instruments brand CC1101 transceiver. Moreover, the communication circuit 258 may be configured to encode, decode, encrypt, decrypt, upconvert, downconvert, and/or otherwise process or perform operations on an electronic signal intended for transmission to and/or received from the power management component 213, or other components of the remotely adjustable gastric banding system. The communication circuit 258 is coupled to the communication antenna 260.

The communication antenna 260 is configured to facilitate one-way and/or two-way communications between the external power component 217 and the power management component 213 and/or other components of the remotely adjustable gastric banding system. In certain exemplary embodiments, the communication antenna 260 comprises a meandering monopole antenna, a loop antenna, a dipole antenna, or other suitable antenna. In various example embodiments, the communication antenna 260 is configured to be operative at frequencies between about 402 MHz and about 406 MHz, and in other example embodiments, at frequencies between about 360 MHz and about 440 MHz. Moreover, the communication antenna 260 may be operative over any suitable frequency and/or range of frequencies, as desired.

In an example embodiment, various portions of the external power component 217 may suitably be combined and/or integrated, for example, on a single chip. For example, the microcontroller 256 and the communication circuit 258 may be integrated onto a single chip or other electronic component. The switchable tuning circuit 252 and the driver circuit 254 may be similarly combined. Moreover, various portions of the external power component 217 may comprise multiple electronic components, chips, couplings, and/or the like, as suitable to enable a desired function of the external power component 217.

Continuing to reference FIG. 2A, in an example embodiment, the power management component 213 generally comprises an inductive power receiver 270, a voltage rectifier 272, a voltage conditioner 274, a sampling circuit 276, a voltage regulator 278, a microcontroller 280, a communication circuit 282, a communication antenna 284, a positive high voltage generator 286, and a negative high voltage generator 288. The power management component 213 may utilize switched-mode power supplies or other suitable components to generate a bipolar voltage. Various components, for example, low on-resistance transistors, a Cockcroft-Walton cascade, a Villard cascade, and/or other components and/or configurations of components may also suitably utilized within the power management component 213.

In one example embodiment, the power management component 213 is configured to utilize electromagnetic energy transmitted via the electromagnetic power signal 219 to generate a power signal having a positive voltage of at least about 60 volts and a negative voltage of at least about 60 volts. The power signal from the power management component 213 may be utilized to power one or more components of the remotely adjustable gastric banding system, for example, pumps, sensors, valves, and/or the like. In one embodiment, the power signal from the power management component 213 is used to operate the high precision pump unit 114 in order to adjust the constriction of the gastric band 106. Power to the power management component 213 is delivered via the electromagnetic communication signal 221 for reception at the inductive power receiver 270.

In an example embodiment, the inductive power receiver 270 comprises an inductive antenna. The inductive power receiver 270 may be configured to receive power via mutual induction, resonant induction, and/or any other suitable wireless power transmission method and/or technique. Furthermore, the inductive power receiver 270 may be operative over a range of frequencies. In various example embodiments, the inductive power receiver 270 is operative over a range from about 400 kHz to about 27 MHz. Moreover, the inductive power receiver 270 may be operative at any suitable frequency to receive power from an external source, for example, the external power component 217. The inductive power receiver 270 is coupled to the voltage rectifier 272.

In an example embodiment, an alternating current produced in the inductive power receiver 270 by operation of the external power component 217 is rectified to direct current within the voltage rectifier 272. Thereafter, direct current is output by the voltage rectifier 272 for use in other portions of the power management component 213. The voltage rectifier 272 may comprise any suitable diodes, bridges, chips, and/or other components, as known in the art. The voltage rectifier 272 is coupled to the voltage conditioner 274 and the sampling circuit 276.

The voltage conditioner 274 is configured to modify, process, and/or otherwise affect the rectified power delivered by the voltage rectifier 272. For example, the voltage conditioner 274 may be configured with various filters, regulators, diodes, and/or any other suitable components, as desired, in order to reduce and/or eliminate transient voltage spikes, line noise, and/or the like, associated with the output of the voltage rectifier 272. The voltage conditioner 274 is coupled to the sampling circuit 276 and the voltage regulator 278.

Moreover, in certain example embodiments, the functions of the voltage conditioner 274 and the voltage regulator 278 may be performed by a single component, e.g., a combined conditioner/regulator.

The sampling circuit 276 is configured to assess, measure, monitor, and/or characterize the power received at the power management component 213 from the external power component 217. For example, the sampling circuit 276 may be configured to measure and/or calculate an amount of power received at the inductive power receiver 270, and to report the amount of power received to the microcontroller 280. In an exemplary embodiment, the sampling circuit 276 comprises an analog-to-digital converter (ADC) operating at a target sampling frequency, for example, a frequency at least twice as large as the frequency of the electromagnetic power signal 219. However, the sampling circuit 276 may operate at any suitable frequency, which may be higher than, equal to, or lower than the frequency of the electromagnetic power signal 219. The sampling circuit 276 couples to the microcontroller 280 to allow the microcontroller 280 to change operating parameters, for example, based on the level of the analog voltage reported by the ADC. In one example embodiment, the sampling circuit 276 comprises a successive-approximation ADC. In another example embodiment, the sampling circuit 276 comprises a delta-sigma ADC. Moreover, the sampling circuit 276 may comprise any suitable ADC or other similar components, as desired.

In certain exemplary embodiments, the sampling circuit 276 is integrated with and/or comprises a portion of the microcontroller 280.

The voltage regulator 278 receives an input from the voltage conditioner 274 and is configured to provide one or more substantially fixed output voltages for use by other components of the power management component 213. For example, the voltage regulator 278 provides a Vcc voltage for use by the microcontroller 280, for example, 5 volts, 3.3 volts, 1.8 volts, and/or the like. The voltage regulator 278 also provides a voltage for use by the positive high voltage generator 286 and a voltage for use by the negative high voltage generator 288. The voltages provided by the voltage regulator 278 to other components of the power management component 213 may be different from one another; alternatively, at least two of the voltages provided by the voltage regulator 278 may be the same. Moreover, the voltage regulator 278 may provide a single, uniform output voltage. The voltage regulator 278 may comprise a linear regulator, a switching regulator, and/or combinations of the same, or any other suitable voltage regulation components. The voltage regulator 278 is coupled to the microcontroller 280, the positive high voltage generator 286, and the negative high voltage generator 288.

Moreover, in certain example embodiments, the functions of the sampling circuit 276 and the voltage regulator 278 may be performed by a single component, e.g., a combined sampler/regulator.

The microcontroller 280 governs operation of the power management component 213. In an exemplary embodiment, the microcontroller 280 comprises a programmable microcontroller, for example, one or more of the following: a microcontroller from the Texas Instruments brand MSP430 or CC430 families; a microcontroller from the MicroChip brand PIC16 or PIC18 families; or a microcontroller from the Freescale brand MC9 family. Moreover, the microcontroller 280 may be configured to monitor, control, and/or otherwise govern operation of the power management component 213, for example, responsive to user input received at the remote controller 115, responsive to information received from the external power component 217 via the electromagnetic communication signal 221, and/or the like.

The microcontroller 280 is configured to execute instructions received from the external power component 217. For example, upon receipt of an instruction from the external power component 217, the microcontroller 280 is configured to cause the power management component 213 to deliver an output power and/or control signal to operate the high precision pump unit 114 in order to at least partially inflate and/or deflate the gastric band 106. The microcontroller 280 may be configured with suitable control, monitoring, and/or reporting functionality through embedded software. Moreover, the microcontroller 280 may also be re-programmed after implantation of the power management component 213, for example, via information delivered via the electromagnetic communication signal 221. The microcontroller 280 is coupled to the communication circuit 282, to the positive high voltage generator 286, and to the negative high voltage generator 288.

The communication circuit 282 is configured to send and receive signals to and from the external power component 217 via the communication antenna 284. In an exemplary embodiment, the communication circuit 282 comprises a low-power RF transceiver, for example, a Texas Instruments brand CC1101 transceiver. Moreover, the communication circuit 282 may be configured to encode, decode, encrypt, decrypt, upconvert, downconvert, and/or otherwise process or perform operations on an electronic signal intended for transmission to and/or received from the external power component 217. The communication circuit 282 is coupled to the communication antenna 284.

The communication antenna 284 is configured to facilitate one-way and/or two-way communication between external power component 217 and the power management component 213 and/or other components of an adjustable gastric banding system. In certain exemplary embodiments, the communication antenna 284 comprises a meandering monopole antenna, a loop antenna, a dipole antenna, or other suitable antenna. In various example embodiments, the communication antenna 284 is configured to be operative at frequencies between about 402 MHz and about 406 MHz, and in other example embodiments at frequencies between about 360 MHz and about 440 MHz. Moreover, the communication antenna 284 may be operative over any suitable frequency and/or range of frequencies, as desired.

Figure 2B:
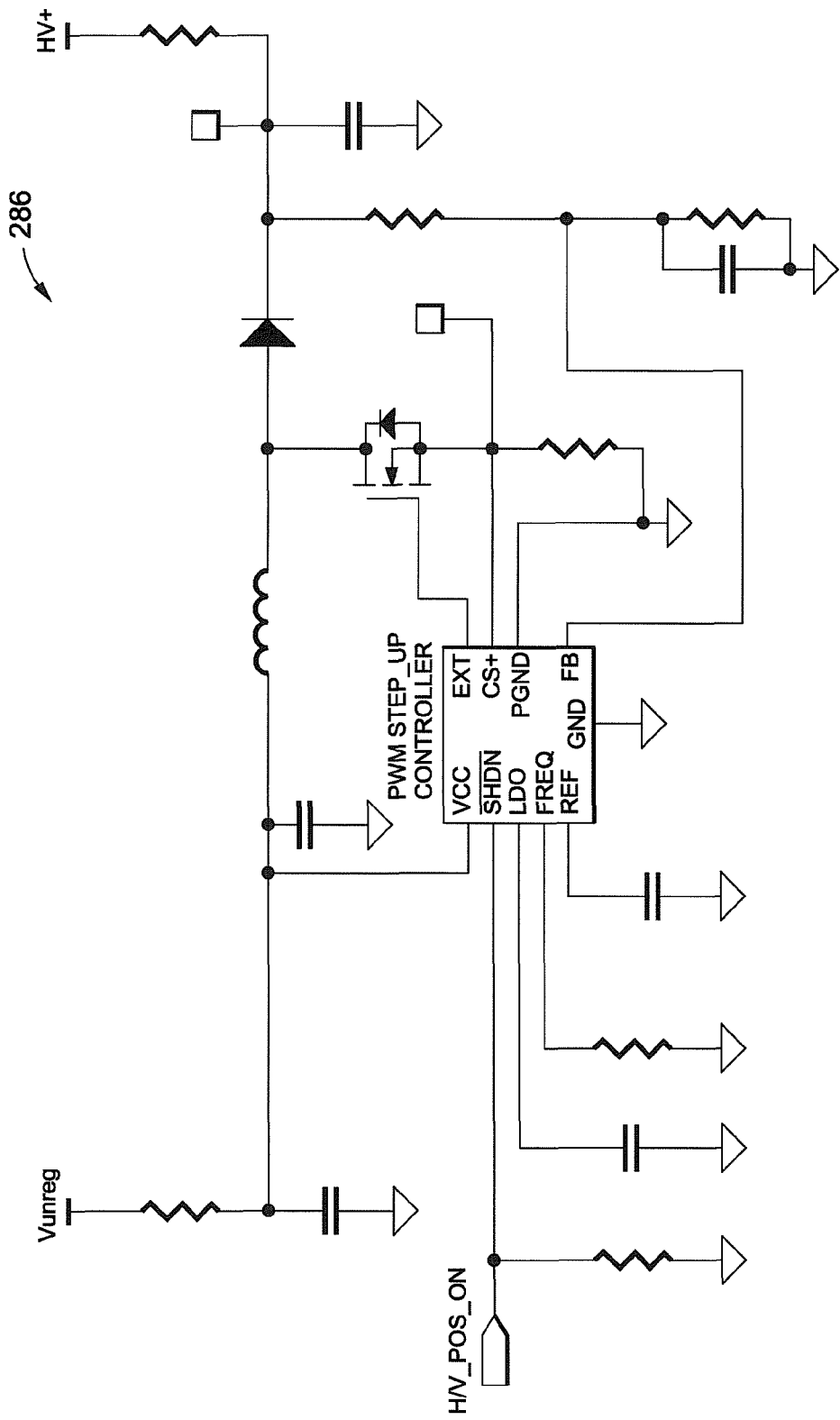
FIG. 2B illustrates a circuit diagram of a positive high voltage generator according to an embodiment of the present invention.

FIG. 2B illustrates an exemplary circuit diagram of the positive high voltage generator 286. With reference again to FIG. 2A and with additional reference to FIG. 2B, the positive high voltage generator 286 is configured to generate a positive voltage for use to operate one or more components of the remotely adjustable gastric banding system, such as the high precision pump unit 114. In an exemplary embodiment, the positive high voltage generator 286 comprises a DC-DC controller, for example, a Maxim brand MAX668 DC-DC controller. The positive high voltage generator 286 may be configured to generate a desired positive voltage, for example, a voltage in excess of 5 volts, 12 volts, 24 volts, 60 volts, and/or other suitable positive voltages, as desired. In one embodiment, the positive high voltage generator 286 utilizes a charge pump with feedback-controlled pulse width modulation.

In order to reduce and/or eliminate electromagnetic interference normally associated with switching power supplies, the positive high voltage generator 286 may be temporarily shut down and/or disabled by the microcontroller 280. For example, the positive high voltage generator 286 may be disabled during a period of sensitive measurement associated with one or more components of the remotely adjustable gastric banding system. Additionally, the positive high voltage generator 286 may be disabled when not in use in order to minimize the current drawn by the positive high voltage generator 286.

Figure 2C:
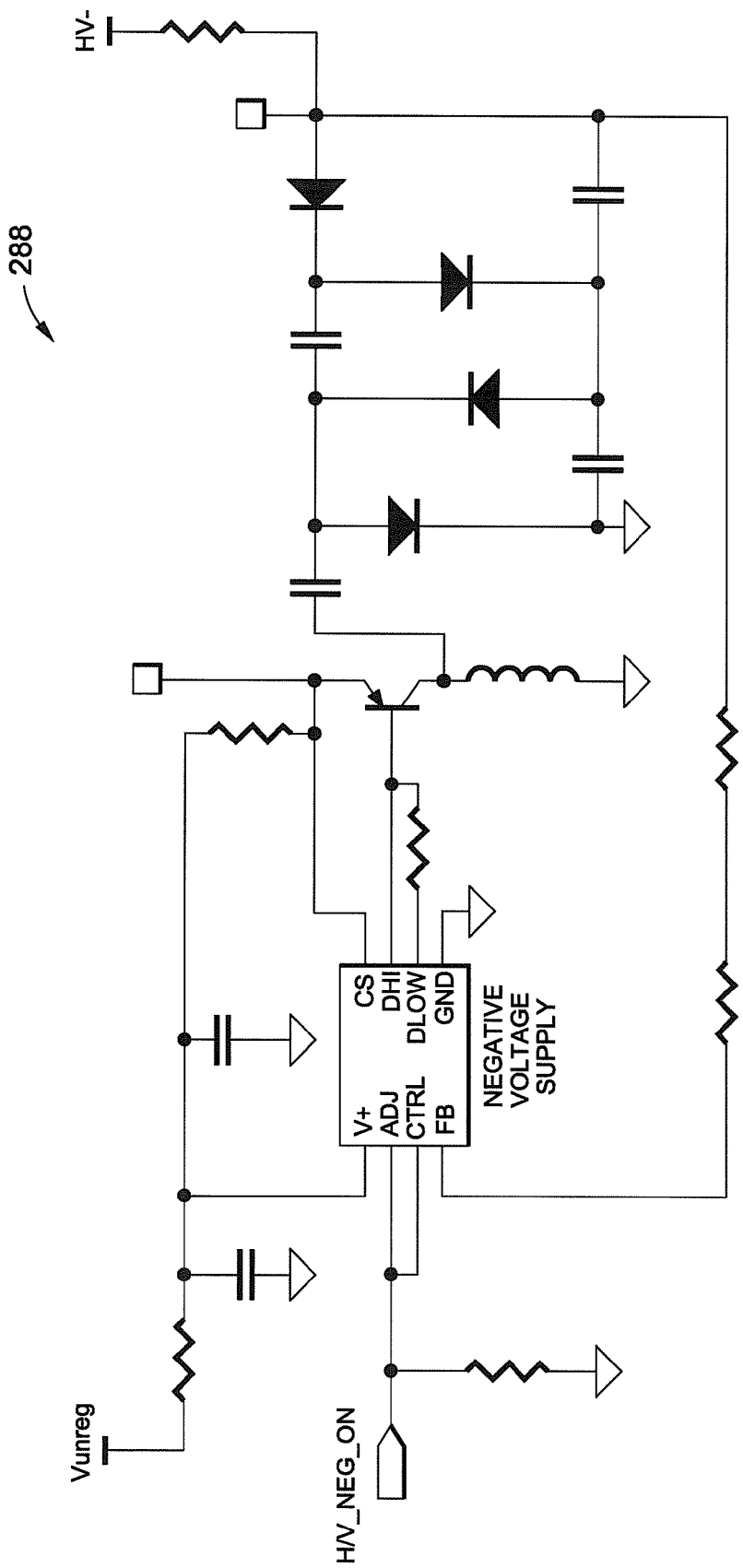
FIG. 2C illustrates a circuit diagram of a negative high voltage generator according to an embodiment of the present invention.

FIG. 2C illustrates an exemplary circuit diagram of the negative high voltage generator 288. With reference again to FIG. 2A and with reference now to FIG. 2C, the negative high voltage generator 288 is configured to generate a negative voltage for use to operate one or more components of the remotely adjustable gastric banding system, such as the high precision pump unit 114. In an exemplary embodiment, the negative high voltage generator 288 comprises a negative bias supply, for example, a Maxim brand MAX749 adjustable LCD bias supply. The negative high voltage generator 288 may be configured to generate a desired negative voltage, for example, a negative voltage in excess of 5 volts, 12 volts, 24 volts, 60 volts, and/or other suitable negative voltages, as desired. In one embodiment, the negative high voltage generator 288 utilizes a charge pump with feedback-controlled pulse width modulation and feedback-controlled pulse frequency modulation.

In order to reduce and/or eliminate electromagnetic interference normally associated with switching power supplies, the negative high voltage generator 288 may be temporarily shut down and/or disabled by the microcontroller 280. For example, the negative high voltage generator 288 may be disabled during a period of sensitive measurement associated with one or more components of the remotely adjustable gastric banding system. Additionally, the negative high voltage generator 288 may be disabled when not in use in order to minimize the current drawn by the negative high voltage generator 288.

In one example embodiment, the power management component 213 provides power to other components of the remotely adjustable gastric banding system via an output from the positive high voltage generator 286 and an output from the negative high voltage generator 288.

In another example embodiment, the power management component 213 provides power to other components of the remotely adjustable gastric banding system by providing a monopolar high voltage (for example, an output from the positive high voltage generator 286). A switching scheme may be employed to alternate the ground and voltage connections on the other component (e.g., the high precision pump unit 114 and/or the like).

In yet another example embodiment, various components of the power management component 213 may be configured with switches to dissipate existing charge. In this manner, energy efficiency may be improved by dissipating existing charge of a first polarity which may be stored in the components, and then recharging the components with voltage of an opposite polarity.

In an example embodiment, various components of the power management component 213 may suitably be combined and/or integrated, for example, on a single chip. For example, the sampling circuit 276 and the voltage regulator 278 may be integrated onto a single chip or other electronic component. The microcontroller 280 and the communication circuit 282 may be similarly combined. Moreover, in some example embodiments, all components of the power management component 213 may be integrated onto a single chip, which may comprise an application specific integrated circuit (ASIC), a field-programmable gate array (FPGA), and/or other suitable chip, as desired.

The power management component 213 and/or components thereof may be compatible with magnetic resonance imaging (MRI), which is much safer for a patient than exposure to X-ray radiation. In one example embodiment, the systems and apparatus described herein are configured and structured to be compatible with MRI, or MRI safe, at magnetic field strengths of up to about 1.5 Tesla. For example, the power management component 213 may be entirely inductively powered. The power management component 213 may utilize no permanent magnets, no long metallic wires or leads, and a minimal or negligible amount of ferrous or ferromagnetic material. The power management component 213 may be substantially free of or contain substantially no ferromagnetic materials. Substantially no ferromagnetic materials refers to materials containing less than about 5%, preferably less than about 1% or 0.1% (w/w) of ferromagnetic material. The resulting systems are thus MRI safe given standard specifications regulating translational and rotational attraction, MRI heating, and imaging artifacts. All materials selected for the systems are preferably selected to be compatible and safe in an MRI environment.

Additional details regarding adjustable gastric banding systems and exemplary components thereof may be found in Birk, U.S. Patent Application Publication No. 2009/0270904, and Birk, U.S. Patent Application Publication No. 2007/0156013, each of which are commonly assigned herewith and incorporated in their entirety herein by this specific reference.

The systems and apparatus described herein may be suitable for use with the remote controller unit 115, which provides access to system data and functions. The remote controller unit 115 may be an external, handheld, reusable battery-powered device, or any other suitable electronic device. The remote controller unit 115 can be made of any rugged material, including polypropylene, cyclicolefin co-polymer, nylon, and other compatible polymers and the like. The remote controller unit 115 is not implanted within the patient, so hermetic sealing of the unit is not required. However, the remote controller unit 115 is preferably at least water resistant, if not waterproof, and may be cleaned using standard hospital disinfectants without damage to the unit. The external power component 117 may be coupled to and/or integrated with the remote controller unit 115.

Further, the remote controller unit 115 is configured with a user interface including at least one display 116 and at least one user input 118. In some example embodiments, the display 116 and the user input 118 are combined in the form of a touch screen with a color display. In other embodiments, the display is grayscale. The remote controller unit 115 permits a clinician or a patient to interact with the remotely adjustable gastric banding system, for example, by navigating through menu driven screens used for data entry, data collection, and control of other components of the remotely adjustable gastric banding system.

The remote controller unit 115 is capable of communicating with the pressure sensor 108, the power management component 113, the high precision pump unit 114, and/or other components of the remotely adjustable gastric banding system. "Capable of communicating" as used herein refers to the ability of the remote controller unit 115 to establish communications with other components, yet still have the ability to break communication and the systems described herein still function. To establish communication, in one example embodiment, once the remote controller unit 115 is initialized, a display shows a searching query for nearby compatible components, for example, the power management component 113, the high precision pump unit 114, the pressure sensor 108, and/or the like. As the remote controller unit 115 is brought into range of a compatible component, a symbol displays the strength of the communication link. Once stable communications have been acquired, the display may show the serial number or other identifying indicia of the component or system so a clinician can verify they have the appropriate patient records in hand.

Via the remote controller unit 115, the clinician can obtain information from and/or issue commands to other components of the remotely adjustable gastric banding system. For example, if the patient requires a tightening of the gastric band 106, the clinician can enter the amount of the desired volume increase. If the patient requires a loosening of the gastric band 106, the clinician can enter the amount of the desired volume decrease. Current and/or logged pressure readings from the pressure sensor 108 may similarly be obtained. The remote controller unit 115 can also display the current and/or desired volume within the gastric band 106 and indicate the new volume as the gastric band 106 fills or drains.

To verify an appropriate adjustment has been made to the system, the clinician can set the remote controller unit 115 into a pressure monitor mode and request that the patient drink water. The display may show a real time graph of one or more pressure readings measured within the remotely adjustable gastric banding system, for example, by one or more of the pressure sensors 108. This diagnostic tool may show higher pressures and warning messages if the gastric band 106 has been over-tightened.

The remote controller unit 115 can synchronize and charge when coupled with a charging cradle or docking station. This docking station provides the ability to recharge a battery for the remote controller unit 115, and may also provide a link to download information to a personal computer such as the adjustment history of a patient. Other data that can be stored on the remote controller unit 115 and downloaded from the power management component 113, the high precision pump unit 114 and/or the pressure sensor 108 includes, but is not limited to, serial number, gastric band size, patient information, gastric band volume, current pressure, historical pressure, firmware version, patient adjustment history, and power received by the power management component 113. This data can be downloaded directly to a patient tracking database for ease of tracking.

Any data stored on the remote controller unit 115, on the pressure sensor 108, on the power management component 113, on the external power component 117, and/or on the high precision pump unit 114 can be electronically secured. In other words, security measures can be put in place to keep the data confidential, including communication between the high precision pump unit 114 and the remote controller unit 115, communication between the high precision pump unit 114 and the pressure sensor 108, and/or other communications between various components of the gastric banding system. Security measures can include computer generated algorithms that prevent intrusion by outside parties.

In an example embodiment, the power management component 113 is a passive device configured to be powered by and/or communicate with the remote controller unit 115 when it is in close proximity. For example, in one example embodiment, the remote controller unit 115 may be configured to power and communicate with the power management component 113 at a distance less than about 8 inches, preferably less than about 4 inches (about 10.2 cm) of tissue plus about 4 inches, preferably about 2 inches (about 5.1 cm) of air. Moreover, power and communications can be tailored to transmit over longer distances, or can be tailored to have the remote controller unit 115 placed on the skin adjacent to the power management component 113.

The remote controller unit 115 can inductively power and telemetrically control the power management component 113. The remote controller unit 115 may be configured to provide continuous power to the power management component 113. In an example embodiment, a dedicated microcontroller within the remote controller unit 115 monitors the amount of power that is transmitted. Further, a power management system may be implemented to optimize energy transmission between the remote controller unit 115 and the power management component 113 relative to their separation distance. For example, the power transmission may automatically decrease as the remote controller unit 115 is moved closer to the power management component 113, and may be increased as the distance is increased. This reduces wasted energy, and energy exposure to the patient.

The systems and apparatus described herein use common surgical techniques to place the components in their respective positions within a patient. The surgical techniques may be identical or similar to those used in the placement of conventional gastric banding systems. For example, the gastric band 106 may be placed around the stomach using laparoscopic techniques, as known to those of skill in the art. Like a conventional access port, the high precision pump unit 114, the power management component 113, and/or the access port 102 may be sutured onto the rectus muscle sheath or any other conveniently accessible muscle. For example, in order to achieve a secure attachment of the high precision pump unit 114, it may be sutured to the rectus muscle and remain securely attached for forces below about 6 pound-force (about 26.6 Newtons), and preferably below about 3 pound-force (about 13.3 Newtons). The tubing 104 passes through the rectus muscle into the peritoneal cavity.

The systems and apparatus of the present invention further allow for remotely monitored pressure and controlled adjustment without needles, non-invasively, by using the remote controller unit 115. Also, should the remote controller unit 115 be unavailable, damaged, out of power, or if one or more of the power management component 113 or the external power component 117 are inoperative, or in the event of an emergency, an adjustment of the gastric band 106 can be performed invasively using a needle. For example, by using the access port 102 illustrated in FIG. 1B, a clinician can choose to use a standard needle for adjustments. If any of the electronics associated with the systems and apparatus described herein become inoperative, the access port 102 can be used to add or remove the fluid from the gastric band 106. The access port 102 and a syringe or needle can be used to adjust the gastric band 106.

The systems described herein generally function as follows. A clinician uses the external power component 117, which may be integral to or comprise a portion of the remote controller unit 115, to activate the power management component 113. Responsive to a command from the clinician, the power management component 113 may then cause the high precision pump unit 114 to activate to adjust the gastric band 106.

The remote controller unit 115 may also be utilized to query one or more of the pressure sensors 108. The pressure sensors 108 are activated responsive to an energy pulse from the remote controller unit 115. The pressure sensors 108 may then take pressure readings, store pressure values or other information, and/or transmit current and/or historical pressure values or other information to the remote controller unit 115. Updated configuration information, command information, control information, diagnostic information, reset information, and/or other suitable information may be sent to and/or from the remote controller unit 115 and the pressure sensor 108 and/or the power management component 113.

Responsive to information from the pressure sensor 108, the power management component 113 and/or other suitable information or operating parameters, the remote controller unit 115 may subsequently and/or simultaneously communicate with and/or power the power management component 113, for example, in order to power the high precision pump unit 114 in order to adjust the gastric band 106. In an example embodiment, the remote controller unit 115 communicates simultaneously with the pressure sensor 108 and/or the power management component 113 and/or the high precision pump unit 114 in order to monitor pressure changes in the gastric banding system during filling and/or draining of the gastric band 106. In one example, the total power consumed by the pressure sensor 108, the power management component 113, the high precision pump unit 114, and all other inductively powered components of the remotely adjustable gastric banding system during simultaneous operation thereof is less than 1 watt. In another example, the total power consumed is less than 700 milliwatts.

Further, the inductive powering of the power management component 113 utilizes energy passed through the body tissue 122. Since the body tissue 122 absorbs a portion of the energy passing through it, the heating of the body tissue can be proportional to the total energy transferred. To ensure that the systems meet standards to minimize tissue heating (below 2° C. above body temperature per ISO 45502), the power management component 113 described herein may be designed to use very little power to generate suitable voltages to power other components of the remotely adjustable gastric banding system, for example, less than about 500 milliwatts, or preferably less than about 250 milliwatts, and does not cause excessive heating of the body tissue 122.

The systems described herein are configured to meet at least one safety specification. For example, in the event of any failure of the systems, either no change in the gastric band 106 tightness or a loosening of the gastric band 106 results. Further, the power management component 113 and the high precision pump unit 114 are biocompatible for long term implantation, and the remote controller unit 115 is biocompatible for transient use both per ISO 10993. The systems are designed to have no significant interaction or interference with other electronics in any of the following modalities: implantable energy sources such as defibrillators and pacemakers; internal energy sources such as electrosurgical instruments; external energy sources such as ultrasound, x-rays and defibrillators; and radiofrequency signals such as pacemaker programmers and neuron-stimulators.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the present invention.

Groupings of alternative elements or embodiments of the present invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the present invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. An implantable device that uses inductive coupling to adjust a circumference of a gastric band, the implantable device comprising:
    an antenna that receives power from a remote device and that is configured to be tuned to vary the power received from the remote device;
    a converter that converts the power to a low voltage direct current;
    a charge pump that converts the low voltage direct current to a voltage signal, wherein the charge pump is turned off using a telemetric signal received from the remote device; and
    an electromechanical device, coupled to the gastric band, that increases and decreases the circumference of the gastric band using the voltage signal received from the charge pump, wherein the electromechanical device is powered solely by the voltage signal from the charge pump, and the electromechanical device excludes and is not configured to be powered by or coupled to an implantable energy source.

2. The implantable device of claim 1, wherein the antenna is an inductively-coupled antenna.

3. The implantable device of claim 1, wherein the voltage signal comprises at least one of a monopolar voltage signal, a bipolar voltage signal, and combinations thereof.

4. The implantable device of claim 1, wherein the voltage signal has positive and negative voltage values.

5. The implantable device of claim 1, wherein the voltage signal includes a positive voltage value of at least 60 volts and a negative voltage value of at least 60 volts.

* * * * *